United States Patent
Mosnier et al.

(10) Patent No.: US 10,624,677 B2
(45) Date of Patent: Apr. 21, 2020

(54) VERTEBRAL OSTEOSYNTHESIS EQUIPMENT

(71) Applicant: Medicrea International, Rillieux la Pape (FR)

(72) Inventors: Thomas Mosnier, Anthon (FR); David Ryan, Collonges au Mont d'Or (FR)

(73) Assignee: MEDICREA INTERNATIONAL, Rillieuz la Pape (FR)

( * ) Notice: Subject to any disclaimer, the term of this patent is extended or adjusted under 35 U.S.C. 154(b) by 624 days.

(21) Appl. No.: 15/289,702

(22) PCT Filed: Apr. 17, 2015

(86) PCT No.: PCT/IB2015/052822
§ 371 (c)(1),
(2) Date: Oct. 10, 2016

(87) PCT Pub. No.: WO2015/159271
PCT Pub. Date: Oct. 22, 2015

(65) Prior Publication Data
US 2017/0172631 A1 Jun. 22, 2017

(30) Foreign Application Priority Data
Apr. 17, 2014 (FR) .................................... 14 53464

(51) Int. Cl.
*A61B 17/70* (2006.01)
*A61B 17/86* (2006.01)

(52) U.S. Cl.
CPC ...... *A61B 17/7041* (2013.01); *A61B 17/7043* (2013.01); *A61B 17/7056* (2013.01); *A61B 17/8665* (2013.01)

(58) Field of Classification Search
CPC .................................................. A61B 17/7041
See application file for complete search history.

(56) References Cited

U.S. PATENT DOCUMENTS 5,584,833 A * 12/1996 Fournet-Fayard .......................... A61B 17/7037 606/278
5,653,710 A * 8/1997 Harle ................. A61B 17/7002 606/308

(Continued)

FOREIGN PATENT DOCUMENTS

FR 2765093 A1 12/1998
FR 2989264 A1 10/2013

(Continued)

OTHER PUBLICATIONS

The International Search Report and the Written Opinion for PCT/IB2015/052822, ESA/EPO, Berlin, Germany, dated Oct. 22, 2015.

*Primary Examiner* — Jan Christopher L Merene
(74) *Attorney, Agent, or Firm* — M&B IP Analysts, LLC

(57) ABSTRACT

Vertebral osteosynthesis equipment is disclosed, including a connection assembly with a connection piece of open type and a mating component piece positioned one with respect to the other. The connection piece includes a hole, where the mating piece is dimensioned to be engaged in the interior of the hole in a fit adjusted manner and is slidable within the hole. The connection piece is assembled to the mating component piece in separated apart position based on a force that is less than a clamping force exerted by a nut to be screwed on to a proximal threaded pin of an anchoring member that can be tightened so as to bring the connection piece and the mating component piece in a close position.

11 Claims, 3 Drawing Sheets

(56) References Cited

U.S. PATENT DOCUMENTS

| | | | |
|---|---|---|---|
| 5,810,818 A * | 9/1998 | Errico | A61B 17/7056 606/276 |
| 8,197,517 B1 | 6/2012 | Lab et al. | |
| 2002/0169450 A1 | 11/2002 | Lange | |
| 2007/0233069 A1* | 10/2007 | Young | A61B 17/7032 606/288 |
| 2011/0245877 A1* | 10/2011 | Pisharodi | A61B 17/7001 606/268 |
| 2013/0072991 A1 | 3/2013 | Rathbun | |
| 2015/0025576 A1* | 1/2015 | Taylor | A61B 17/7035 606/250 |
| 2016/0183983 A1* | 6/2016 | Heflin | A61B 17/7037 606/266 |
| 2017/0020578 A1* | 1/2017 | Mosnier | A61B 17/7055 |

FOREIGN PATENT DOCUMENTS

| | | |
|---|---|---|
| WO | 1998055038 B1 | 1/1999 |
| WO | 2011043805 A1 | 4/2011 |
| WO | 2012060868 A1 | 5/2012 |

\* cited by examiner

VERTEBRAL OSTEOSYNTHESIS EQUIPMENT

BACKGROUND

The present invention relates to a vertebral osteosynthesis equipment.

A vertebral osteosynthesis equipment includes, in a manner that is well known per se:
- at least one rigid rod intended to be extending along several vertebrae, and in general two rods intended to be placed on either side of the spinous processes of the vertebrae;
- bone anchoring members, such as screws or laminar hooks, intended for anchoring the rod or rods to the vertebrae to be treated; each bone anchoring member has a proximal threaded pin and a support surface;
- connection pieces to be used for connecting the rod or rods to the bone anchoring members, each connection piece having a hole for the engagement thereof on to the proximal threaded pin of a bone anchoring member and a receiving channel for the engagement of an aforementioned rod; and
- nuts intended to be screwed on to the proximal threaded pins of the bone anchoring members in order to tighten the connection pieces against the said support surfaces.

A known device of this type is described in particular in the published patent application No. WO 98/55038; in this device, each connection piece is of the "closed" type, that is to say it has a closed portion for delimiting the said receiving channel for receiving one aforementioned rod. Such a rod can thus only be engaged axially in this channel.

Known equipments also include, in particular as detailed in the published patent applications Nos U.S. 2013/072991 A1, U.S. 2002/169450 A1or FR 2 765 093 A1, devices comprising connection assemblies with each including a connection piece of "open" type, that is to say, having a curved portion that is adapted to only partially enclose a rod as mentioned above, and a mating component piece that, in a closer position relative to the curved portion, makes it possible to close the channel delimited by this curved portion in order to retain a rod engaged in the said channel. The connection piece and the mating component piece are provided with holes for the engagement thereof on to the proximal threaded pin of the anchoring member and comprise positioning means to ensure the positioning of one in relation to the other in a mounting position in which these holes come to be coincident with each other.

The vertebral osteosynthesis equipment according to the aforementioned prior art documents have the disadvantage of not being very easy to implement as implants due to the fact that the connection pieces and the mating component pieces are to be set in place and positioned one after another, at the bottom of the cavity, and because they have reduced dimensions, which make the risk of their escape quite high. The impact of these drawbacks are felt all the more given that the successive assembly and disassembly of the rods and connection assemblies must be carried out in order to test the curvature of the vertebral rods during the surgical intervention so as to assess whether the form and shape of the rods are such as to allow for the desired correction or adjustment to be obtained.

SUMMARY

The object of the present invention is thus to remedy these essential drawbacks.

The concerned equipment includes:
- at least one rigid rod intended to be extending along several vertebrae, and in general two rods intended to be placed on either side of the spinous processes of the vertebrae;
- bone anchoring members, such as pedicular screws or laminar hooks, intended for anchoring the said rod to the vertebrae to be treated; at least one bone anchoring member has a proximal threaded pin and a support surface;
- connection assemblies to be used for connecting the rod to the bone anchoring members; at least one connection assembly includes a connection piece of "open" type, that is to say, having a curved portion that delimits a receiving channel for receiving the rod and which is adapted to only partially enclose the rod, and a mating component piece that is movable relative to this said connection piece; the mating component piece is movable between a separated apart position relative to the said curved portion, in which it does not hinder the transverse engagement of the rod in the receiving channel, and a closer position relative to the said curved portion, in which the mating component piece closes the receiving channel and retains the rod in this channel; the connection piece and the mating component piece are provided with holes for engagement thereof on to the said proximal threaded pin and comprise positioning means to ensure their proper positioning in relation to one another in a mounting position in which these holes come to be coincident with each other; and
- at least one nut intended to be screwed on to the said proximal threaded pin so as to clamp the connection piece and the mating component piece between itself and the said support surface and to thereby bring the connection piece and the mating component piece into the said closer position;

the said positioning means include:
- the hole in the said connection piece;
- a portion of the said mating component piece, dimensioned so as to be engaged in the interior of this hole in a fit adjusted manner and so as to be slidable in this hole;

and the said connection assembly comprises:
- assembly means for assembling of the connection piece to the mating component piece, thereby causing the connection assembly to have a unitary structure, and
- maintaining means for maintaining in place the said mating component piece in the said separated apart position, allowing for the maintaining in place of this mating component piece relative to the connection piece, this maintaining in place being brought about based on a force that is less than the clamping force exerted by the nut during the screwing of this nut on to the said proximal threaded pin.

Thanks to use of the said assembly means, the connection assembly has a unitary structure that enables the easy handling of the equipment according to the invention, without requiring the repeated installing in place and removal of separate pieces, having reduced dimensions. The maintaining means provide the ability to maintain in place the mating component piece in the said separated apart position, in order to facilitate the successive installing in place and removal of the rod or rods from the connection assemblies. When it comes to carrying out the final mounting of the equipment, the nuts are screwed on, which removes the maintained hold created by the maintaining means and makes it possible to bring the mating component pieces into the closer position relative to the curved portions, and to thereby bring about the closing of the engaging channels for engaging the rod.

The said assembly means and the said maintaining means may be constituted by means of the appropriate sizing of the hole of the connection piece and by the appropriate sizing of the said portion of the mating component piece which would be such that there would exist friction between this connection piece and this portion, thereby enabling the assembly and maintenance in place of these pieces; according to one preferred embodiment of the invention, however, the said assembling means and the said maintaining means are formed by respective engagement portions of the connection piece and of the said portion of the mating component piece brought into engagement with one another, and which are capable of being brought out of engagement when the said nut is screwed on.

According to a first possible embodiment of the invention, in this case, the said assembling means and the said maintaining means comprise a collar flange formed on to one among the connection piece and the mating component piece and by a groove provided in the other piece, the collar flange being capable of being positioned and retained in the groove in the absence of the clamping force exerted by the nut, and being capable of being extracted from this said groove during the screwing of the nut.

Preferably,
the said groove is formed in the connection piece, and
the said portion of the mating component piece is formed by a series of snapping teeth disposed in a circle, forming together, externally, the said collar flange, the said teeth being resiliently movable between a radially outer position, in which the said collar flange is capable of being engaged in the said groove, and a radially inner position, in which the said teeth are deflected in a manner so as not to be an impediment to the sliding of the mating component piece in the hole that the connection piece includes.

In addition to maintaining of the mating component piece in the separated apart position, this embodiment provides for the bearing of the teeth against the connection piece along a reduced surface area, and therefore with limited friction, which allows for a relatively easy return, if necessary, of the mating component piece and of the mating component piece in the separated apart position.

According to a second possible embodiment of the invention,
one among the connection piece and the mating component piece has an elongated aperture formed parallel to the direction of movement of these pieces during their passage from the said separated apart position to the said closer position; this elongated aperture is delimited by longitudinal edges and at least one of the longitudinal edges has a protuberance projecting out towards the interior of the elongated aperture; this protuberance subdivides the elongated aperture into a hold maintaining housing and a sliding portion;
the other among the connection piece and the mating component piece includes a pin engaged through the elongated aperture and capable of sliding therein from the hold maintaining housing up to the sliding portion, by crossing over by force the said protuberance during this sliding.

In the separated apart position where the connection piece and the mating component piece are separated, the pin is located in the hold maintaining housing, which ensures the assembly of the connection piece and the mating component piece and maintains in place these pieces in the separated apart position. When the nut is screwed on to the said threaded pin and moves these two component pieces relative to one another, the pin crosses over the protuberance by force, in a manner such that the hold enabled by this pin and this protuberance is removed and that the two pieces can be brought in said closer position.

Preferably, the two longitudinal edges delimiting the elongated aperture each have a protuberance and the two protuberances are located so as to be facing one another.

A clear hard point is thus formed.

Preferably, the two longitudinal edges delimiting the elongated aperture each have two protuberances and each protuberance is located so as to be facing a protuberance situated on the opposite edge, the two pairs of protuberances delimiting an intermediate hold maintaining zone, thus making it possible to maintain the pin in place therein, and therefore to maintain the connection piece and the mating component piece in an intermediate position between the separated apart position and the closer position mentioned above.

Preferably, the hold maintaining housing is fit adjusted to the pin in a manner so as to keep this pin immovable within it, and therefore to keep the mating component piece immovable relative to the connection piece.

Preferably, the mating component piece and the connection piece form stop surfaces which precisely determine the said closer position of these two component pieces.

Any risk of the excessive tightening of the nut, which is likely to cause deterioration in the mating component piece, is thus eliminated, and the said stop surfaces in addition provide the ability to distribute the clamping force exerted by the nut.

Preferably, the mating component piece forms a lateral extension that makes it possible to close the receiving channel for receiving the rod and this lateral extension has a cavity in the form of a hollow cylinder formed on it.

The invention will be better understood and other characteristic features and benefits thereof will become apparent by means of the description that follows, which is provided with reference made to the accompanying diagrammatic drawing; this drawing shows, by way of non-limiting examples, two possible embodiments of relevant equipment.

DESCRIPTION OF THE PREFERRED EMBODIMENTS

Figure 7:
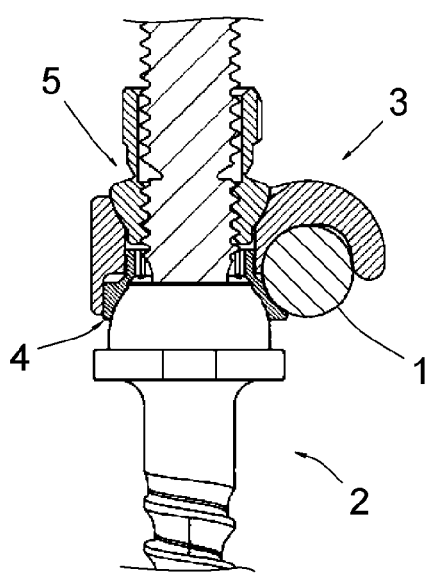
FIG. 7 is a view of the equipment which is similar to that in FIG. 6, wherein the nut is shown in a fully tightened position.

FIG. 7 shows a rod 1, a pedicular screw 2, a connection piece 3, a mating component piece 4, and a nut 5 that are included in a vertebral osteosynthesis equipment.

In a general manner, this equipment includes:
two rods 1 intended to be placed on either side of the spinous processes of the vertebrae to be treated;
a plurality of pedicular screws 2, intended to be anchored in the pedicles of these vertebrae;
a plurality of connection pieces 3 and mating component pieces 4, intended to be installed in place on the screw 2; and
a plurality of nuts 5 to be used for clamping the connection assemblies formed by the connection pieces 3 and the mating component pieces 4 on to the screws 2, as is visible in this FIG. 7.

The rods 1 are of the conventional type, consisting of metal rods that are to be shaped according to the correction of the vertebral column to be achieved. In the illustrated example, the said rods 1 have a substantially circular cross-section.

Figure 5:
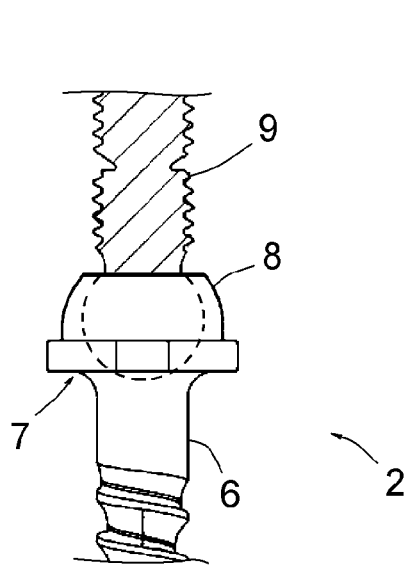
FIG. 5 is a partial view, from the side, of a pedicular screw that this equipment also includes.

Each pedicular screw 2, as represented, is of the type called "polyaxial", that is to say comprising (see FIG. 5) a threaded bone anchoring base 6, a head 7 forming a surface 8 which constitutes a support for the said connection assembly formed by the pieces 3 and 4, and a proximal threaded pin 9 connected in an articulated manner relative to the base 6. In the example shown, this articulated joint is obtained in the manner described in the published patent application No. WO 98/55038, that is to say by means of a ball joint formed by a sphere (represented in broken lines in FIG. 5), that is integrally attached to the pin 9. This sphere is engaged in a cavity provided in the head 7 and is retained in this cavity by means of crimping of the wall forming the said support surface 8. This wall is shaped in a manner so as to present a peripheral surface formed as an hemisphere.

With reference to FIGS. 1 to 4, it is apparent that the connection piece 3 comprises a body 3a and, on one side thereof, a curved portion 3b.

The body 3a has:
a hole 10 which passes right through it from one side to the other, thereby enabling the engagement of the connection piece 3 on the said proximal threaded pin 9,
a bottom recess 11 that delimits a flat surface 12 around the bottom opening of the hole 10, and
a groove 13 that is coaxial with the hole 10, arranged in a bottom area of this hole 10, close to the recess 11.

It will be understood that the term "bottom" is used to refer to the side of the connection piece 3 that is situated closest to the support surface 8 when the connection piece 3 is in place on the screw 2.

Figure 1:
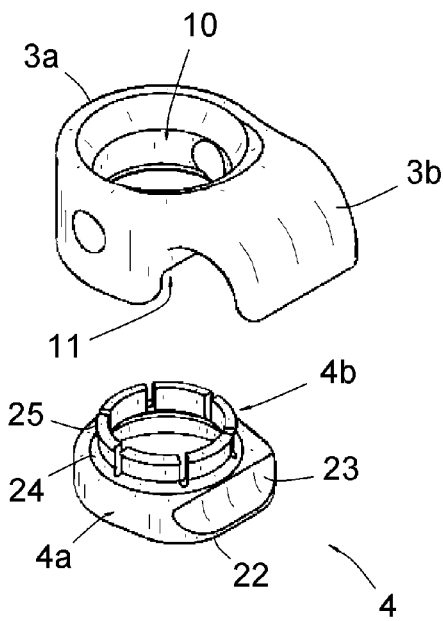
FIG. 1 is a perspective view of a connection piece and a mating component piece which this equipment comprises, according to a first embodiment.
Figure 2:
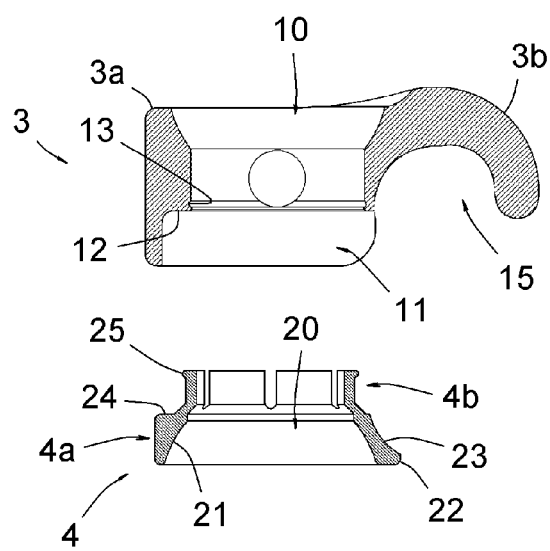
FIG. 2 is a cross section view of these component pieces taken through the axis of holes that the connection piece and the mating component piece include.
Figure 3:
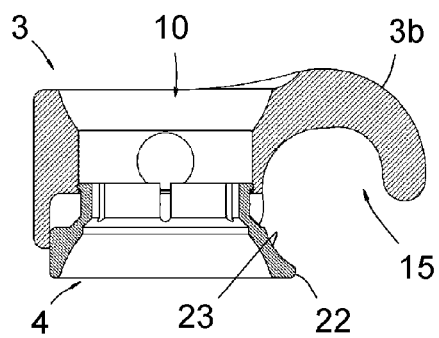
FIG. 3 is a view of these pieces which is similar to that in FIG. 2, shown in a separated apart position wherein the mating component piece is separated apart relative to the connection piece.
Figure 4:
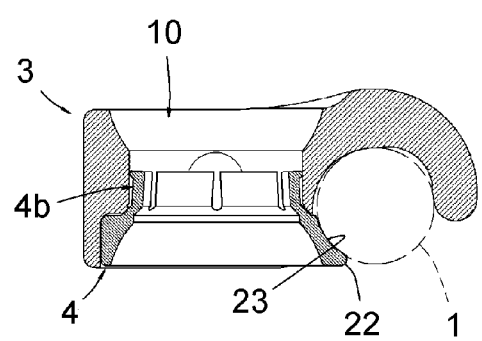
FIG. 4 is a view of these pieces which is similar to that in FIG. 3, shown in a closer position wherein the mating component piece and the connection piece are locked together relative to each other; this figure also shows, in broken lines, a rod that the equipment also includes.
Figure 6:
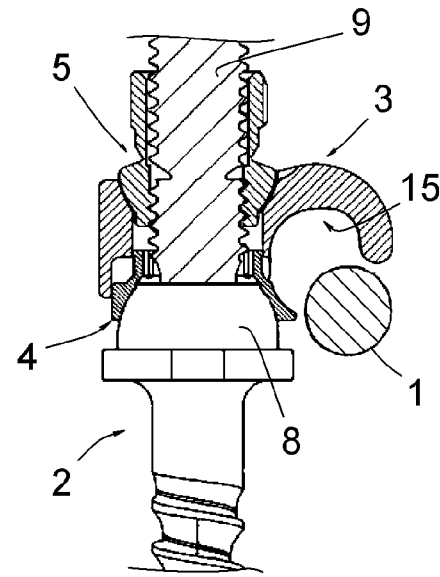
FIG. 6 is a view of this screw and the said component pieces set in place on the screw, in the said separated apart position, with this position allowing for the engagement of the rod that the equipment includes, in a receiving channel that is formed by the connection piece; a nut that the equipment also includes is also represented.

The groove 13 is rounded and has a shallow depth, in a manner such that a snapping flange 25 described farther down, designed to be engaged in it as shown in FIGS. 3 and 6, may be extracted from it, as may be seen in FIGS. 4 and 7, under the effect of the clamping force exerted on the connection piece 3 by the nut 5.

The portion 3b of the connection piece 3 is curved in a manner so as to delimit a receiving channel 15 for receiving a rod 1, but only partially encircles this rod, over about 180°, as can be seen in FIG. 4. The connection piece 3 is therefore a type of connection piece referred to as "open" type, that is to say, capable of receiving the rod 1 by means of transverse engagement of the rod.

The mating component piece 4 has a hole 20 passing right through it, which enables its engagement on to the said proximal threaded pin 9, and includes a bottom portion 4a and an top portion 4b.

The bottom portion 4a is in the form of a flared skirt, internally forming a hemispherical surface 21 for bearing against the support surface 8, and forming on one side a lateral closing extension 22 for closing the receiving channel 15. A cavity in the form of a portion of a hollow cylinder 23 having the same radius as the rod 1, is provided on this lateral extension 22.

The said bottom portion 4a forms, at its top end, a planar surface 24 adapted to meet the surface 12 in the closer position shown in FIG. 4 wherein the pieces 3 and 4 are locked together.

The top portion 4b is formed by a series of snapping teeth disposed in a circle, each having an exterior terminal bead. The beads of the different teeth together constitute the snapping flange 25 mentioned above. As it is to be understood with reference to FIGS. 2 and 3, these teeth are resiliently movable between a normal position that is radially external, as may be seen in FIG. 2, and a radially internal position, as may be seen in FIG. 4, in which the teeth are resiliently deflected towards the interior of the hole 20.

The top portion 4b is designed to be engaged in the hole 10 of the connection piece 3, by internal deflection of the teeth, until the latching of the collar flange 25 into the groove 13. This latching defines the aforementioned separated apart position, in which the lateral extension 22 is at a distance from the free end of the curved portion 3a which is sufficient to enable a transverse engagement of the rod 1, as may be seen in FIG. 6.

The internal deflection of the snapping teeth also allows for the said top portion 4b to be engaged in the hole 10 beyond the groove 13 and to slide in the latter up until the closer position shown in FIG. 4. In this closer position, the lateral extension 22 comes to close the receiving channel 15, in a manner such that the rod 1 engaged in this channel cannot be extracted from the channel, as can be seen in FIG. 7.

The nut 5 is of a known type and is thus not described in details.

In practice, the screws 2 (FIG. 5) are set in place in the pedicles of the vertebrae to be treated and then the assemblies of pieces 3/pieces 4 (with each piece 4 in the separated apart position in relation to each piece 3) are engaged on to the pins 9 of these different screws 2, until the support surfaces 21 of the pieces 4 come up against the support surfaces 8 of the screws 2.

The nuts 5 are then screwed on to the pins 9 up to a position of contact with the pieces 3, in a manner so as to ensure the maintenance in position of the pieces 4 against the support surfaces 8 (FIG. 6); in this position, each rod 1 can be easily engaged in the channels 15 and be removed from the latter, in order to carry out the successive operations of curving and testing of the rods 1.

When the rods 1 are completely set in the requisite shape and formed in a manner so as to make it possible to ensure the desired correction of the vertebrae, the screws 5 are tightened in a manner so as to move the pieces 3 in the direction of the pieces 4 and, by bringing close together the extensions 22 and the free ends of the curved portions 3b, to close the channels 15 around each rod 1 (FIG. 7).

Figure 8:
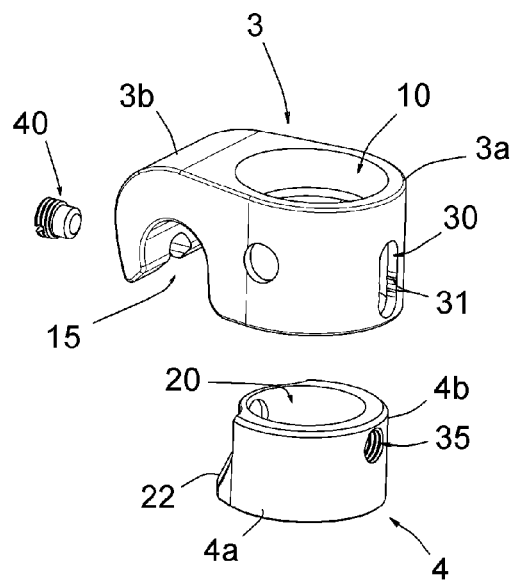
FIGS. 8 and 9 are perspective views, on two different angles, of a connection piece and of a mating component piece that this equipment includes, according to a second embodiment.
Figure 8A:
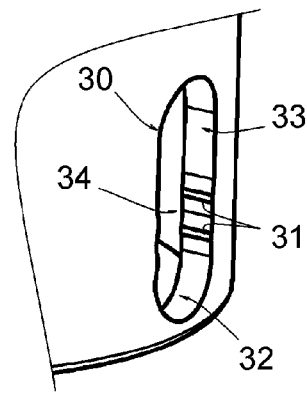
FIG. 8A is a partial view of the connection piece as shown in FIG. 8, at a greatly enlarged scale.
Figure 9:
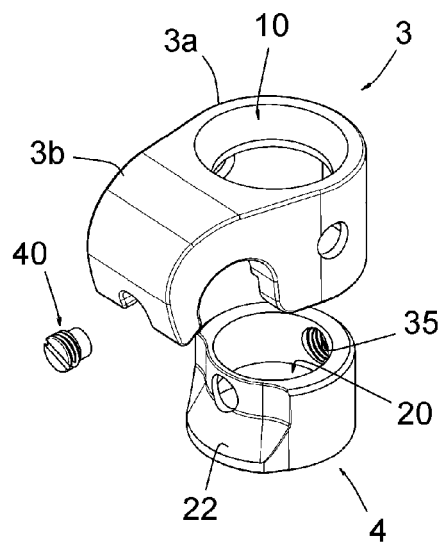

FIGS. 8 and 9 show the second embodiment of the pieces 3 and 4. For the purposes of simplification, the parts or elements that have already been described with reference to FIGS. 1 to 7, which happen to be found on these pieces, are denoted by the same numerical references and will not be described again.

In this case, the connection piece 3 has an elongated aperture 30 formed through its body 3a, parallel to the direction of movement of the mating component piece 4 in relation thereto at the time of the passing of this mating component piece from the said separated apart position to the said closer position. This elongated aperture 30 is delimited by longitudinal edges each having two protuberances 31, with each protuberance 31 being positioned so as to be facing another protuberance 31 situated on the opposite edge.

Each protuberance 31 is formed by inclined walls joining together so as to form a rounded top edge and is adapted to be crossed by the body of a pin 40 described further below.

The lower pair of protuberances 31 delimits, with the bottom portion of the elongated aperture 30, a hold maintaining housing 32 having appropriate dimensions that are fit adjusted to those of the body of the pin 40. The upper pair of protuberances 31 delimits, with the top portion of the elongated aperture 30, a sliding portion 33, in which the body of the pin 40 is capable of sliding. The two pairs of protuberances 31 delimit between them an intermediate hold maintaining zone 34, capable of receiving the body of the pin 40 in a fit adjusted manner.

The mating component piece 4 has a circular top portion 4b that is adapted to be received in a fit adjusted manner in the hole 10 of the connection piece 3 but with the capability to slide in this hole. This top portion 4b has a threaded hole 35 that comes to be coincident with the elongated aperture 30 in the mounting position and receiving the pin 40 screwed into it.

This pin 40 has the aforementioned body, which is cylindrical and smooth, and which is intended to be received and slide in the elongated aperture 30. It also has a threaded head that is intended to be screwed into the hole 35.

The connection piece 3 in addition has a notch formed in the curved portion 3b, coaxially to the hole 35, and the mating component piece 4 has a hole formed on its side diametrically opposite to the hole 35, which allows for the engagement of the pin 40 in these pieces 3, 4 and the screwing of the head of this pin 40 into the threaded hole 35.

Figure 10A:
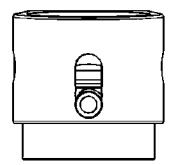
FIGS. 10A and 10B are respectively profile and side views of these pieces, wherein the pieces are in a separated apart position.
Figure 10B:
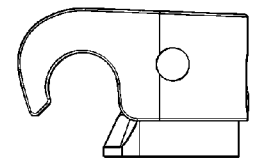
Figure 11A:
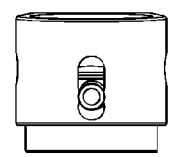
FIGS. 11A and 11B are views of these pieces which are similar to those in FIGS. 10A and 10B, with the pieces being in an intermediate position.
Figure 11B:
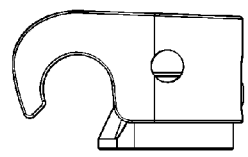
Figure 12A:
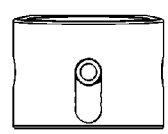
FIGS. 12A and 12B are views of these component pieces which are similar to those in FIGS. 11A and 11B, with the component pieces being in a closer position.
Figure 12B:
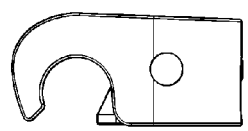

In practice, in the space apart position of the lateral extension 22 and of the curved portion 3b (see FIGS. 10A and 10B), the body of the pin 40 is held in the hold maintaining housing 32, which maintains the pieces 3 and 4 in this position. When the nut 5 is screwed on to the pin 9, this body of the pin 40 comes to cross the lower pair of protuberances 31 and be placed in the intermediate hold maintaining zone 34, which makes it possible to maintain the pieces 3 and 4 in the intermediate position shown in FIGS. 11A and 11B; this intermediate position provides the practitioner with the ability to indeed ensure the correct mounting of the rod 1 before the final mounting is carried out. The additional screwing of the nut 5 enables the body of the pin 40 to cross over the upper pair of protuberances 31 and to be placed in the sliding portion 33, which makes it possible to bring the pieces 3 and 4 into the closer position shown in FIGS. 12A and 12B.

As is apparent from the foregoing, the invention provides a vertebral osteosynthesis equipment that presents the decisive advantage of making it possible to facilitate the successive operations of curving and positioning of the rods 1 while also obtaining a good degree of certainty of resistance over the course of time of the connection created between a rod 1 and a connection assembly.

The invention has been described here above with reference to the embodiments provided by way of examples. However, it goes without saying that it is not limited to these embodiments but indeed extends to all other embodiments covered by the claims appended herewith.

What is claimed is:

1. Vertebral osteosynthesis equipment, including:
   at least one rigid rod intended to be extending along several vertebrae;
   bone anchoring members intended for anchoring the at least one rigid rod to the vertebrae to be treated wherein at least one of the bone anchoring members has a proximal threaded pin and a support surface;
   connection assemblies to be used for connecting the at least one rigid rod to the bone anchoring members, wherein at least one connection assembly includes a connection piece of "open" type having a curved portion that delimits a receiving channel for receiving the at least one rigid rod and which is adapted to only partially enclose the at least one rigid rod, and a mating component piece that is movable relative to the connection piece, wherein the mating component piece is movable between a separated apart position relative to the curved portion, in which it does not hinder the transverse engagement of the at least one rigid rod in the receiving channel, and a closer position relative to the curved portion, in which the mating component piece closes the receiving channel and retains the at least one rigid rod in the channel; wherein the connection piece and the mating component piece are each provided with a hole for engagement thereof onto the proximal threaded pin and comprise an assembly means to ensure proper positioning in relation to one another in a mounting position in which the holes come to be coincident with each other; and
   at least one nut intended to be screwed on to the proximal threaded pin so as to clamp the connection piece and the mating component piece between the at least one nut and the support surface and to thereby bring the connection piece and the mating component piece into the closer position, wherein said assembly means include:
   an engagement portion of the mating component piece, dimensioned so as to be engaged in the interior of the hole of the connection piece in a fit adjusted manner and so as to be slidable in the hole of the connection piece; and the connection assembly comprises:
- a maintaining means for maintaining in place the mating component piece in the separated apart position, formed by engaging parts of the connection piece and of the mating component piece, allowing for the maintaining in place of the mating component piece relative to the connection piece, the maintaining in place being brought about based on a force that is less than the clamping force exerted by the at least one nut during the screwing of the at least one nut on to the proximal threaded pin, such that the engaging parts forming said maintaining means are capable of being brought out of engagement when the at least one nut is screwed on.

2. Equipment according to claim 1, characterized in that the engaging parts comprise a collar flange formed on the mating component piece and by a groove provided in the connection piece, the collar flange being capable of being positioned and retained in the groove in the absence of the clamping force exerted by the one nut, and being capable of being extracted from the groove during the screwing of the one nut.

3. Equipment according to claim 2, characterized in that:
- the engagement portion of the mating component piece is formed by a series of snapping teeth disposed in a circle, forming together, externally, the collar flange, the teeth being resiliently movable between a radially outer position, in which the collar flange is capable of being engaged in the groove, and a radially inner position, in which the teeth are deflected in a manner so as not to be an impediment to the sliding of the mating component piece in the hole formed in the engagement portion of the connection piece.

4. Equipment according to claim 1, characterized in that the maintaining means comprise:
- an elongated aperture formed in the connection piece, the elongated aperture being formed parallel to the direction of movement of the connection piece and the mating component piece during passage of the connection piece and the mating component piece from the separated apart position to the closer position; the elongated aperture is delimited by two longitudinal edges and at least one of the longitudinal edges has a protuberance projecting out towards the interior of the elongated aperture; the protuberance subdivides the elongated aperture into a hold maintaining housing and a sliding portion;
- a pin included in the mating component piece, the pin being engaged through the elongated aperture and capable of sliding into the latter from the hold maintaining housing up to the sliding portion, by crossing over by force the protuberance during the sliding.

5. Equipment according to claim 4, characterized in that each of the two longitudinal edges delimiting the elongated aperture has two protuberances and the two protuberances are located so as to be facing one another.

6. Equipment according to claim 5, characterized in that each of the two protuberances is located so as to be facing a protuberance situated on the opposite edge, and each protuberance is formed by two pairs of protuberances delimiting an intermediate hold maintaining zone, thus making it possible to maintain the pin in place therein, and therefore to maintain the connection piece and the mating component piece in an intermediate position between the separated apart position and the closer position.

7. Equipment according to claim 4, characterized in that the hold maintaining housing is fit adjusted to the pin in a manner so as to keep the pin immovable within it, and therefore to keep the mating component piece immovable relative to the connection piece.

8. Equipment according to claim 1, characterized in that the mating component piece and the connection piece form stop surfaces which precisely determine the closer position of the two pieces.

9. Equipment according to claim 1, characterized in that the mating component piece forms a lateral extension that makes it possible to close the receiving channel for receiving the at least one rigid rod and the lateral extension has a cavity in the form of a portion of a hollow cylinder formed on it.

10. Equipment according to claim 1, characterized in that the equipment includes two rigid rods intended to be placed on either side of the spinous processes of the vertebrae.

11. Equipment according to claim 1, characterized in that the bone anchoring members are at least one of: pedicular screws and laminar hooks.

* * * * *